United States Patent
Sato et al.

(10) Patent No.: US 6,565,751 B2
(45) Date of Patent: May 20, 2003

(54) BIOREACTOR CARRIER, PROCESS FOR PRODUCING THE CARRIER AND METHOD FOR USING THE SAME

(76) Inventors: Takaya Sato, Chiba-ken (JP); Tsutomu Uehara, Chiba-ken (JP); Hiroshi Yoshida, Chiba-ken (JP); Mitsugu Kotani, Chiba-ken (JP)

(*) Notice: Subject to any disclaimer, the term of this patent is extended or adjusted under 35 U.S.C. 154(b) by 54 days.

(21) Appl. No.: 09/867,613

(22) Filed: May 31, 2001

(65) Prior Publication Data

US 2002/0005381 A1 Jan. 17, 2002

(30) Foreign Application Priority Data

May 31, 2000 (JP) ......................................... 2000-161976

(51) Int. Cl.⁷ .................................................. C02F 3/00
(52) U.S. Cl. ........................................ 210/616; 210/150
(58) Field of Search ................................ 210/615–618, 210/150

(56) References Cited

FOREIGN PATENT DOCUMENTS

| EP | 0829536 A1 | 3/1998 |
|---|---|---|
| EP | 0864540 A2 | 9/1998 |
| EP | 0864540 A3 | 4/1999 |

OTHER PUBLICATIONS

Patent Abstracts of Japan, Publ. No. 09051794—Feb. 25, 1997.

*Primary Examiner*—Chester T. Barry

(57) ABSTRACT

There are disclosed a bioreactor carrier comprising a (A) water swellable thermoplastic resin, preferably water swellable thermoplastic polyurethane resin and a (B) compatible resin with the resin as the component (A), and as the case may be, a (C) inorganic filler, characterized in that the degree of volumetric swelling of said carrier is controlled within the range of 120 to 3000%, and that the specific gravity of said carrier on swelling in water is controlled within the range of 1.02 to 2.12; a process for producing the bioreactor carrier; and a process for denitrifying treatment of organic waste water which comprises nitrifying and denitrifying nitrogen components in the organic waste water with microbes by using the above bioreactor carrier. The bioreactor carrier has high physical strength, can be readily produced and uniformly fluidized in a reactor, and enables microbial and enzymatic reactions to be effectively performed.

12 Claims, 1 Drawing Sheet

BIOREACTOR CARRIER, PROCESS FOR PRODUCING THE CARRIER AND METHOD FOR USING THE SAME

BACKGROUND OF THE INVENTION

1. Field of the Invention

The present invention relates to a bioreactor carrier, a process for producing the carrier and a method for using the same. More particularly, it pertains to a bioreactor carrier which is imparted with water swelling properties, a degree of volumetric swelling or a degree of volumetric swelling along with a specific gravity, each being controlled within a specific range, and high physical strength; enables microbial reactions and enzymatic reactions to be effectively performed; and moreover is readily producible, to a process for producing the carrier in high efficiency, and to a method for effectively carrying out denitrifying treatment for organic waste water with microbes by the use of the above-stated carrier.

2. Description of the Related Arts

The carriers to be employed in bioreactors can be broadly classified into porous carriers and gel carriers. Examples of the porous carriers include those made of polyurethane, cellulose, polypropylene, polyvinyl formal, ceramic etc., respectively. Because of their being porous, the carriers have a large surface area and in the majority of cases, are employed in a state of bindingly immobilized animal cells, plant cells, microbes and/or protozoans onto the porous surfaces thereof.

However, the aforesaid porous carriers suffer from various disadvantages and drawbacks as described hereunder. Polyurethane and polypropylene porous bodies, due to their being hydrophobic, have inferior fluidity in water and moreover, make it difficult for animal cells, plant cells, microbes and/or protozoan to be bonded thereonto. Cellulose porous bodies are subject to attack by microbe, whereby their service life is unfavorably shortened. With regard to polyvinyl formal porous bodies, an industrial process for producing the same is not yet established. Ceramic porous bodies can not be fluidized in water due to their high specific gravity, thus inevitably restricting the usage.

On the other hand, there are known as gel carriers, those made of polyacrylamide, polyethylene glycol, polyvinyl alcohol and alginic acid, thermoplastic water absorbing bodies, etc., respectively {refer to Japanese Patent Application Laid-Open No. 136980/1998 (Heisei-10)}. It is a general practice to use these gel carriers by entrappingly immobilizing animal cells, plant cells, microbes and/or protozoans at the inside of the gel, and alternatively it is possible to use the aforesaid carriers by bindingly immobilizing animal cells, plant cells, microbes and/or protozoans onto the gel surfaces.

The foregoing gel carriers, which highly contain water, generally have high affinity for living matters and at the same time, impart favorable habitat to animal cells, plant cells, microbes and/or protozoans. Nevertheless, the physical strength is not necessarily sufficient in such gel carriers as those made of polyacrylamide, polyethylene glycol, polyvinyl alcohol and alginic acid, which bring about a fear of wear and collapse in the course of service in a reaction tank. In addition, the gel carriers just mentioned, when once molded into a definite shape, can not be changed to an other shape by remelting. Thus, such carriers are generally cut into a required shape in the majority of cases. In fact, the gel carriers suffer from serious disadvantages in that the step of cutting the water-containing and swollen gel into several millimeter sized regular hexahedron requires tremendous labor and period of time with the result that the production thereof becomes extremely intricate and troublesome, thus necessitating markedly long time and high cost in production.

As opposed to the foregoing, thermoplastic water absorbing gel carriers that are typified by thermoplastic water absorbing polyurethane gel carriers are well suited for use as bioreactor carriers owing to such advantages as high physical strength, capability of industrial mass production, capability of adsorbing animal cells, plant cells, microbes and/or protozoans due to their hydrophilicity without deteriorating the physiological activity thereof, favorable resistance to attack by microbes, and the like.

In these thermoplastic water absorbing gel carriers, the degree of volumetric swelling thereof is one of important characteristics. For instance, the degree of volumetric swelling, when being unreasonably low, causes deterioration in microbe adhesion due to unreasonably lowered water absorption, whereas said degree, when being unreasonably high, causes deterioration in the physical strength and/or durability, unendurabilty to practical application and the like. The degree of volumetric swelling depends upon not only the type of thermoplastic resin, but also the type and quantity of an inorganic filler to be added for the purpose of regulating the specific gravity and enhancing the adhesion of microbes to the carriers. Thus, it is extremely important from the industrial point of view to control the degree of volumetric swelling within a desirable range by a simple procedure.

In this connection, utmost importance is attached to the specific gravity of the bioreactor carriers. For instance, the specific gravity thereof, when being close to that of water on attaining steady state of adhesion, binding immobilization of microbes in a reactor, gives rise to such a problem, in the case of fluidizing the liquid to be treated in a reactor for the purpose of reaction, that the carriers are apt to move upwards and difficult to be present in the lower portion, thus causing failure to assure uniform fluidity and deteriorating the efficiency of microbe reaction.

SUMMARY OF THE INVENTION

In such circumstances, an object of the present invention is to provide a bioreactor carrier which is imparted with water swelling properties, a degree of volumetric swelling or a degree of volumetric swelling along with a specific gravity, each being controlled within a specific range, and high physical strength; enables microbial reactions and enzymatic reactions to be effectively performed; and moreover is readily producible, also to provide a process for producing the carrier, and further to provide a method for using the same.

Other objects of the present invention will be obvious from the text of this specification hereinafter disclosed.

In order to achieve the above-mentioned objects, research and investigation were intensively and extensively accumulated by the present inventors. As a result, it has been found that there is obtainable a bioreactor carrier which is imparted with the foregoing characteristics in which a degree of volumetric swelling or a degree of volumetric swelling along with a specific gravity is controlled within a specific range, by blending a water swellable thermoplastic resin such as water swellable thermoplastic polyurethane resin with a compatible resin with the aforesaid resin at the time of molding; and thereafter molding the mixed resin into a desirable form by means of an extruder, or blending the aforesaid water swellable thermoplastic resin with an inorganic filler at the time of producing the resin and/or molding the same; blending the aforesaid water swellable thermoplastic resin with said compatible resin therewith; and thereafter molding the mixed resin into a desirable form by means of an extruder. It has also been found that organic waste water can effectively be subjected to denitrification treatment by using the bioreactor carrier thus obtained as a carrier for immobilizing microbes in nitrifying and denitrifying nitrogenous components in the organic waste water. The present invention has been accomplished on the basis of such findings and information.

That is to say, the present invention provides:

(1) a bioreactor carrier (hereinafter referred to as "bioreactor carrier I") which comprises a (A) water swellable thermoplastic resin and a (B) compatible resin with the resin as the component (A), characterized in that the degree of volumetric swelling of said carrier is controlled within the range of 120 to 3000%;

(2) a bioreactor carrier (hereinafter referred to as "bioreactor carrier II") which comprises a (A) water swellable thermoplastic resin, a (B) compatible resin with the resin as the component (A), and a (C) inorganic filler, characterized in that the degree of volumetric swelling of said carrier is controlled within the range of 120 to 3000%, and that the specific gravity of said carrier on swelling in water is controlled within the range of 1.02 to 2.12;

(3) a process for producing a bioreactor carrier the degree of volumetric swelling of which is controlled within the range of 120 to 3000%, which comprises the steps of blending a water swellable thermoplastic resin with a compatible resin with the aforesaid resin; thereafter heat melting the resultant blend; extruding the molten blend through an extruder into the form of strand; and continuously cutting the strand;

(4) a process for producing a bioreactor carrier the degree of volumetric swelling of which is controlled within the range of 120 to 3000%, and the specific gravity of which on swelling in water is controlled within the range of 1.02 to 2.12, which comprises the steps of blending a water swellable thermoplastic resin with a compatible resin with the aforesaid resin and an inorganic filler; thereafter heat melting the resultant blend; extruding the molten blend through an extruder into the form of strand; and continuously cutting the strand;

(5) a process for producing a bioreactor carrier the degree of volumetric swelling of which is controlled within the range of 120 to 3000%, and the specific gravity of which on swelling in water is controlled within the range of 1.02 to 2.12, which comprises the steps of blending an inorganic filler at the time of producing a water swellable thermoplastic resin from reactants of said resin; blending the resultant blend with a compatible resin with said resin and as the case may be, an inorganic filler; thereafter heat melting the blend thus obtained; extruding the molten blend through an extruder into the form of strand; and continuously cutting the strand; and (6) a process for denitrifying treatment of organic waste water which comprises nitrifying and denitrifying nitrogen components in the organic waste water with microbes by the use of the bioreactor carrier I or II.

Figure 1:
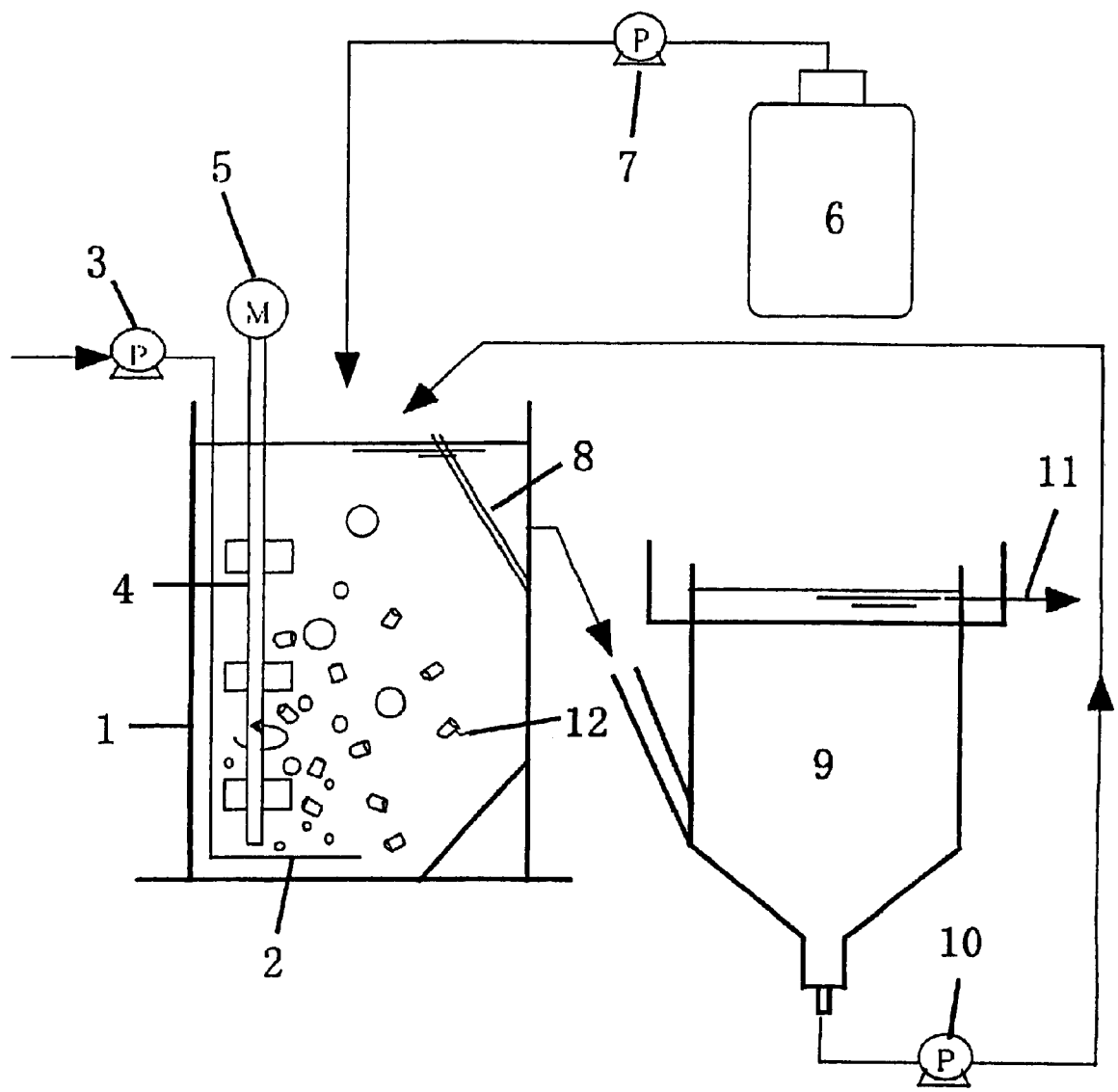
FIG. 1 is a simplified process flow diagram showing one embodiment of a nitrifying denitrifying apparatus according to the present invention, wherein the symbols therein shall have the following designations.

1: biotreatment tank
2: air diffusion pipe
3: aeration pump
4: agitation impeller
5: agitation motor
6: raw water tank
7: liquid transfer pump
8: carrier separation screen
9: settling tank
10: sludge return pump
11: discharge line
12: carrier

DESCRIPTION OF PREFERRED EMBODIMENTS

The bioreactor carrier according to the present invention has two embodiments. Of these, the bioreactor carrier I comprises a (A) water swellable thermoplastic resin and a (B) compatible resin with the resin as the component (A), and the bioreactor carrier II comprises the aforesaid components (A) and (B) and a (C) inorganic filler.

The aforesaid water swellable thermoplastic resin as the component (A) in the bioreactor carriers I and II according to the present invention is exemplified by water swellable thermoplastic polyurethane resin, water swellable thermoplastic polyethylene glycol and the like, among which is particularly preferable water swellable thermoplastic polyurethane resin.

The water swellable thermoplastic polyurethane resin as mentioned above is the polyurethane copolymer comprising a soft segment and a hard segment which are randomly top-to-end bonded by urethane bond. The polyurethane copolymer is synthesized by reacting a bifunctional long chain diol compound, a bifunctional diisocyanate compound and a short chain diol compound.

The soft segment obtained by the reaction between the long chain diol compound and the diisocyanate compound is represented by the following general formula (I):

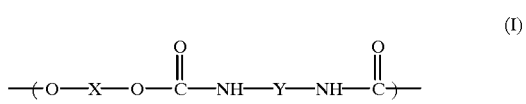

On the other hand, the hard segment obtained by the reaction between the short chain diol compound and the diisocyanate compound is represented by the following general formula (II):

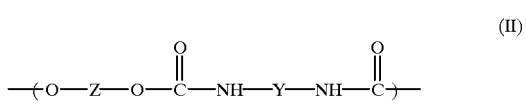

wherein X in the above-mentioned general formulae (I) and (II) is the group which is generated by the reaction of the terminal hydroxy groups of the long chain diol compound with the diisocyanate, and from which the terminal hydroxy groups are removed. It is thought that the molecular weight of X in the formulae exerts a remarkable influence on the degree of swelling and the like of the resin. The molecular weight thereof is in the range of preferably 1,000 to 13,000, more preferably 4,000 to 8,000. The molecular weight of X, when being unreasonably low, causes decrease in the molecular weight of the soft segment and as a result, gives rise to the tendency that the degree of swelling thereof is lowered. On the other hand, the molecular weight of X, when being higher than 13,000, brings about such unfavorable problems as an increase in the viscosity of the reactants and a rise in melting temperature at the time of synthesis. As the long chain diol compound to be used in the present invention, there are preferably usable a water-soluble polyoxyalkylene diol (polyol), and particularly preferably usable a water-soluble ethylene oxide-propylene oxide copolymer polyether-based diol having two terminal hydroxy groups in one molecule or polyethylene glycol. In particular, the content of oxyethylene group is preferably at least 70% by weight, more preferably at least 85% by weight. The content of the oxyethylene group of less than 70% by weight sometimes leads to the resin lowered in the degree of swelling.

In addition, Y in the above-mentioned general formulae (I) and (II) is the group which is generated by the reaction between the diisocyanate compound usually having a number average molecular weight in the range of 100 to 1000 and the hydroxy groups, and from which the isocyanate groups are removed. Specific examples of the diisocyanate compounds that are used in the present invention include tolylene diisocyanate, xylylene diisocyanate, naphthylene diisocyanate, diphenylmethane diisocyanate, biphenylene diisocyanate, diphenyl ether diisocyanate, tolidine diisocyanate, hexamethylene diisocyanate and isophorone diisocyanate.

On the other hand, Z in the foregoing general formula (II) is the group which is generated by the reaction of the terminal hydroxy groups of the short chain diol compound usually having a number average molecular weight in the range of 30 to 400 with the diisocyanate, and from which the terminal hydroxy groups are removed.

Examples of the short chain diol compound to be used in the present invention include ethylene glycol; 1,2-propylene glycol 1,3-propylene glycol; 1,3-butanediol; 2,3-butanediol; 1,4-butanediol; 1,5-pentanediol; 1,6-hexanediol; 2,2-dimethyl-1,3-propanediol; diethylene glycol; dipropylene glycol; 1,4-cyclohaxane dimethanol; 1,4-bis-(β-hydroxyethoxy)benzene; p-xylilenediol; phenyldiethanolamine; methyldiethanolamine; 3,9-bis(2-hydoxy-1,1-dimethylethyl)-2,4,8,10-tetraoxaspiro-(5,5)-undecane; etc.

The ratio of the amount to be used of the long chain diol compound to that of the short chain diol compound can be varied according to the molecular weight of each, desirable physical properties of the resin and the like. Although depending upon the molecular weight of the long chain diol compound, the molar ratio of the long chain diol compound to the short chain diol compound is preferably in the range of 5:1 to 1:2. In the case where the long chain diol compound has a high molecular weight, since the viscosity at the time of synthesizing the thermoplastic resin is prone to become high, it is preferable to decrease the molar ratio of the short chain diol compound which forms the hard segment. However, in order to enhance the degree of volumetric swelling, while maintaining high physical strength, it is preferable to increase the molar ratio thereof. Moreover, it is preferable that the ratio of the number of the isocyanate groups in the diisocyanate compound to the total number of the hydroxy groups in the long chain diol compound and the short chain diol compound (NCO/OH) be in the range of preferably 0.95 to 1.8, more preferably 1.0 to 1.6. It being so, there are usable in the present invention, not only polyurethane copolymer wherein the polymer synthesis reaction has been completed sufficiently, but also incomplete thermoplastic polyurethane, that is, polyurethane copolymers wherein part of active groups such as isocyanate groups remain unreacted, by causing the incomplete polyurethane to be cross-linked after molding.

As the method for producing the thermoplastic polyurethane to be used in the present invention, there are adoptable both a prepolymerization method in which the long chain diol compound and diisocyanate compound are reacted in advance, and thereafter the reaction product is reacted with a short chain diol compound as a chain extender; and a one shot method in which all the starting reactants are simultaneously mixed.

In order to control the degree of volumetric swelling in the bioreactor carriers I and II according to the present invention, there is blended as the component (B), a compatible resin with the water swellable thermoplastic resin as the component (A). By the term "compatible resin" as mentioned herein is meant such a resin that when mixed with the component (A) at any arbitrary proportion and heat melted at a temperature 30° C. higher than the melting point of the resultant mixture, phase separation between the two does not substantially take place.

In the case where the above-mentioned component (A) is water swellable thermoplastic polyurethane resin, the compatible resin as the component (B) is not specifically limited provided that it is thermoplastic and compatible with the water swellable thermoplastic polyurethane resin as the component (A), but may be selected for use from a variety of resins. Specific examples of the compatible resin include polyester-based thermoplastic polyurethane resin, polyether-based thermoplastic polyurethane resin and styrene/butadiene-based elastomer. In the present invention, the compatible resin may be used alone or in combination with at least one other.

The ratio to be contained of the foregoing water swellable thermoplastic resin as the component (A) to the compatible resin as the component (B) is dependent upon the degree of volumetric swelling desirable for the carrier, the degree of volumetric swelling of the water swellable thermoplastic resin to be used, type and quantity of the inorganic filler and the like, and is generally selected so that the ratio by weight of the component (A) to the component (B) falls within the range of 90:10 to 10:90.

The degree of volumetric swelling for the bioreactor carriers I and II according to the present invention, which is represented by the formula (III), is selected in the range of 120 to 3000%. The degree of volumetric swelling, when being less than 120%, causes unreasonably low water absorbability leading to deterioration in the adhesion of microbes, whereas the degree thereof, when being more than 3000%, brings about too lowered strength of the carrier to be practically used. In consideration of the adhesion of microbes, strength of the carrier and the like, the degree of volumetric swelling is preferably in the range of 150 to 1000%.

degree of volumetric swelling in water (%){volume upon complete swelling in water (cm$^3$)/volume on bone dryness (cm$^3$)}× 100    (III)

where the bone dryness is the dryness where the weight does not decrease any longer when dried at 100° C., and the v complete swelling in water is the volume which does not any longer when immersed in pure water at 25° C.

The inorganic filler to be used as the component (C) in the bioreactor carrier II according to the present invention is not specifically limited, but may be selected for use from among barium sulfate, silica, kaolin, quarts sand, diatomaceous earth, barite, talc, alumina, titanium dioxide and iron oxides. Any of the fillers may be used alone or in combination with at least one other. As will be described hereinafter in the production process, the foregoing inorganic filler is blended at the time of producing the water swellable thermoplastic resin and/or at the time of molding for producing the carrier.

It is advantageous to use the inorganic filler which has an average particle diameter in the range of preferably 0.1 to 50 µm, more preferably 0.5 to 30 µm, and which has a specific gravity(true specific gravity, and the same applies hereinafter) of preferably at least 1.5, more preferably in the range of 2.0 to 6.0. Examples of the specific gravity of the inorganic filler to be used in the present invention include 4.3 for barium sulfate; 2.2 for silica; 2.4 for kaolin; 2.56 for quarts sand; 2.15 to 2.31 for diatomaceous earth; 4.5 for barite; 2.6 to 2.8 for talc; 3.99 for alumina; 3.8 to 4.1 for titanium dioxide; and 5.2 for iron oxides.

The content of the aforesaid inorganic filler, although depending upon the desirable specific gravity of the carrier, the type of the compatible resin, the specific gravity of the inorganic filler and the like factors, is selected in the range of generally 1 to 350, preferably 10 to 300 parts by weight per 100 parts by weight of the total sum of the components (A) & (B).

The specific gravity of the bioreactor carrier according to the present invention at the time of swelling in water is controlled within the range of 1.02 to 2.12, preferably 1.02 to 1.85 so as to enable the carrier to uniformly flow in a reactor when the adhesion and binding immobilization of microbes onto the carrier reach a steady state in the reactor.

The specific gravity of the bioreactor carrier at the time of swelling in water is obtained from the weight and the volume of the carrier immersed in pure water at 25° C. by regarding the volume which does not change any longer as the volume on complete swelling in water.

The size and shape of the bioreactor carrier in the present invention are not specifically limited, but the carrier is preferably in the form of regular hexahedron, column, sphere or chip having a uniform size. Specifically preferable forms are a regular hexahedron of 1 to 10 mm in side, a column of 1 to 10 mm in diameter and 1 to 10 mm in length and a sphere of 1 to 10 mm in diameter.

The bioreactor carrier according to the present invention can be efficiently produced by any of the processes according to the present invention as described in the following.

In the first place in producing the bioreactor carrier I, there is used a process wherein the compatible resin is blended and melt molded at the time of molding the water swellable thermoplastic resin so that the resultant carrier has a degree of volumetric swelling set to a desirable value.

On the other hand, in producing the bioreactor carrier II, there are usable: (1) a process wherein the inorganic filler is not added at the time of producing the water swellable thermoplastic resin, but is added along with the compatible resin at the time of molding so that the resultant carrier has a degree of volumetric swelling and a specific gravity upon swelling in water each set to a desirable value, and the mixture is melt molded; (2) a process wherein the inorganic filler is added at the time of producing the water swellable thermoplastic resin so that the resultant carrier has a specific gravity upon swelling in water set to a desirable value, the compatible resin alone is added without adding the inorganic filler at the time of molding so that the resultant carrier has a degree of volumetric swelling set to a desirable value, and the mixture is melt molded; (3) a process wherein the inorganic filler is added at the time of producing the water swellable thermoplastic resin, and is also added along with the compatible resin at the time of molding so that the resultant carrier has a degree of volumetric swelling and a specific gravity upon swelling in water each set to a desirable value, and the mixture is melt molded.

Among the above-mentioned inorganic filler, barium sulfate, kaolin, diatomaceous earth and talc, which usually contain moisture, is preferably dehydrated in advance when added at the time of molding, since the use thereof without dehydration causes a fear of allowing the water swellable resin to swell. Conversely, there is no need to dehydrate any of the fillers when it is added at the time of producing the water swellable resin.

The melt molding is carried out by heat melting the mixture of the components, extruding the same into the form of strand (string) by the use of an extruder, and thereafter cutting the resultant strand into a proper length. For the purpose of enhancing the adhesivity of animal cells, plant cells and microbes, the mixture of the components may be incorporated at the molding time, with inorganic powder such as activated carbon, carbon powder and zeolite in addition to the inorganic filler for modifying the specific gravity. It is also possible to adhere the aforestated inorganic powder to the surface of the strand extruded from the extruder, followed by cutting the same.

The bioreactor carrier according to the present invention which is obtained by the foregoing manner has water swelling properties, high hydrophilicity, properties of accumulating a large quantity of water and high affinity for animal cells, plant cells, microbes and/or protozoans. The bioreactor carrier is used by adding itself in a culture solution and water to be treated in each of which animal cells, plant cells, microbes and/or protozoans are present. Owing to extremely high affinity for living matters the bioreactor carrier allows animal cells, plant cells, microbes and/or protozoans to adhere to the surfaces thereof and proliferate there. In particular, the carrier preferentially allows strongly tacky animal cells, plant cells, microbes and/or protozoans such as ammonium oxidizing bacteria, nitrite oxidizing bacteria, other bacteria for nitrifying ammonia, denitrifying bacteria and filamentous bacteria to adhere and to be bindingly immobilized onto the surfaces thereof.

The bioreactor carrier according to the present invention, which has high shearing resistance, enables efficient agitation by means of an impeller agitator or the like in a state that a large number of animal cells, plant cells, microbes and/or protozoans each serving as biological catalysts are densely immobilized onto the outside surface of the carrier.

In addition, the bioreactor carrier the specific gravity of which is controlled within a specific range enables uniform flow of liquid in a reactor and efficient proceeding of microbe reaction and the like.

In the following, some description will be given of a process for the denitrification treatment of organic waste water according to the present invention.

In a process for the denitrification treatment according to the present invention, use is made of the foregoing bioreactor carrier I or II of the invention as a carrier for immobilizing microbes in the case of nitrifying and denitrifying nitrogenous components in organic waste water.

Ammonia nitrogen in waste water is converted to nitrate nitrogen by the nitrifying bacteria present in activated sludge, while the nitrate nitrogen is converted to gaseous nitrogen by the denitrifying bacteria so that the nitrogen is released into the atmosphere. Due to extremely low breeding rate, nitrifying bacteria are present at a relatively low concentration in suspended microbes group, namely activated sludge. Accordingly, it is impossible for conventional activated sludge process used for general waste water treatment to sufficiently treat ammonia nitrogen.

There exist in activated sludge, such bacteria as having a high breeding rate including BOD digesting bacteria. Thus it follows that BOD digesting bacteria predominantly proliferate to suppress the proliferation of the bacteria having a low breeding rate such as nitrifying bacteria. Consequently, concentration of nitrifying bacteria is low at all times. The bioreactor carrier according to the present invention, when applied to such a system, causes nitrifying bacteria to adhere to even smooth surfaces of the carrier because of their strong tackiness, but causes microbes that are devoid of strong tackiness such as BOD digesting bacteria to be less prone to adhere to smooth surfaces thereof. Consequently, it follows that nitrifying bacteria predominantly proliferate at a high concentration on the surface of the carrier, whereby the ammonia nitrogen is biological treated by the function of the nitrifying bacteria that are proliferated in an extremely efficient manner in a high rate.

It has been confirmed that the bioreactor carrier according to the present invention as described before, which has physical strength and durability that can withstand long-term mechanical agitation and besides, has a high molecular gel structure upon swelling by water absorption, is capable of firmly bndingly immobilizing denitrifying bacteria without installing an uneven portion. In addition, the carrier to be used therein, which is usable in both nitrification step as an aerobic condition and denitrification step as an anaerobic condition, is applicable to various denitrifying activated sludge process. In particular, as compared with a variety of carrier addition recycled nitrifying/denitrification processes in which different carriers are each separately added to an anaerobic tank and an aerobic tank, thus needing countercurrent carrier return in each tank, the process according to the present invention dispenses with distinction between an anaerobic carrier and an aerobic carrier and can perform carrier return in the same manner as nitrifying liquid circulation. What is more, the present process is well suited for various intermittent aeration methods and oxidation ditch methods which have hitherto few examples of adding a carrier.

It is possible in the present invention, for instance, to alternately and repeatedly utilize the same microbe carrier in both the nitrification condition and denitrification condition by a method comprising supplying waste water to be treated continuously or intermittently into a treatment tank, and alternately and repeatedly switching the treatment conditions between the nitrification condition and denitrification condition in a state that the bioreactor carrier is retained in a treatment tank. Thus, there is no restriction on the number of cycles or one cycle time for aerobic and anaerobic cycles.

In an example of adding a microbe carrier to denitrifying activated sludge process unit, there exists the problem in that long-term acclimatization is necessary in the early stage of operation. A solution thereagainst has hitherto been contrived by the use of a entrappingly immobilized carrier. Nevertheless, by using the microbe carrier under both environments including aerobic and anaerobic conditions in the process according to the present invention, it is made possible not only to obtain the microbe carrier imparted with nitrification and denitrification performances, but also to accelerate the rise in an early stages of nitrification and denitrification as compared with the case of acclimatization under either condition only, thereby enabling to shorten the acclimatization term.

When the microbe carrier to be used in the present process is acclimatized in a coexistence of activated sludge under an aerobic condition wherein nitrifying bacteria are proliferated, the nitrifying bacteria are thickly grown on the surface of the carrier, and also protozoa such as ciliates are thickly grown thereon as if they cover the bacteria. It has been found by the present inventors that when the aerobic condition is switched to the anaerobic condition wherein denitrifying bacteria are proliferated, the denitrifying bacteria are adsorbed onto the carrier and thereby are firmly immobilized thereon. It has been confirmed that the phenomenon is not limited to one cycle only, and that both the rises of nitrification and denitrification performances are accelerated at every time the aerobic and anaerobic conditions are alternately repeated. It is considered to be related to cohesive force among the microbes themselves and the denitrifying bacteria being so-called anaerobic.

In the following, the present invention will be described more specifically with reference to the drawings.

FIG. 1 is a simplified process flow diagram showing one embodiment of a nitrifying denitrifying apparatus according to the present invention, wherein a biotreatment tank 1 is equipped inside with an air diffusion pipe 2, an agitation impeller 4 and also a microbe carrier 12. When the inside of the biotreatment tank 1 is brought to an aerobic condition, an aeration pump 3 is operated and air is blown thereinto through the air diffusion Pipe 2 to carry out aeration. When the inside thereof is brought to an anaerobic condition, an agitation motor 5 is operated to operate the agitation impeller 4 so as to mix raw water (waste water to be treated), activated sludge and the carrier 12 in the biotreatment tank 1, while the raw water is allowed to flow into the biotreatment tank 1 from a raw water tank 6 via a liquid transfer pump 7. Irrespective of aerobic or anaerobic condition, organic matters in the raw water are decomposed by the activated sludge in the biotreatment tank 1 and the microbe which is immobilized on the carrier 12, and simultaneously organonitrogen components are decomposed into ammonia nitrogen.

Subsequently upon becoming aerobic state, by the action of the nitrifying bacteria bonded to the carrier 12, the ammonia nitrogen begins to be oxidized and converted to nitrate nitrogen and nitrite nitrogen. Subsequently upon becoming anaerobic state denitrifying bacteria predominate on the surface of the carrier 12, so that the nitrate nitrogen and the nitrite nitrogen are finally decomposed into nitrogen gas by the action of the bacteria. The denitrifying treatment is put into practice by continuously or intermittently supplying the biotreatment tank 1 with raw water and alternately repeating the aerobic state and anaerobic state.

The treated waste water flows out through overflow from the biotreatment tank 1 to a settling tank 9, while the carrier 12 is made to always stay in the biotreatment tank 1 by a carrier separation screen 8, whereby the microbe concentration in the biotreatment tank 1 is maintained at a high level irrespective of the flow rate of the raw water. The activated sludge is separated from the treated waste water by gravity settling in the settling tank 9, and thus only the treated waste water is discharged from a discharge line 11 to the outside of the treatment system. The activated sludge thus settled is returned to the biotreatment tank 1 via a sludge return pump 10 so as to maintain the MLSS concentration therein. The denitrifying bacteria and nitrifying bacteria having a low proliferating rate are maintained at high concentrations by the carrier 12, whereby the sludge control in the present process is more easy than in conventional standard processes.

As described hereinbefore, the process according to the present invention enables nitrification and denitrification of carrier addition system by intermittent aeration without exchanging the microbe carrier. Without being confined to the intermittent aeration, the process is applicable to various recycled nitrifying/denitrification process, oxidation ditch process and the like.

In summarizing the effect of the present invention, the bioreactor carrier is imparted with water swelling properties, a degree of volumetric swelling or a degree thereof along with a specific gravity each controlled within a specific range, and high physical strength; enables microbial reactions and enzymatic reactions to be effectively performed; and moreover is readily producible. The use of the bioreactor carrier as a microbe immobilizing carrier in nitrifying and denitrifying nitrogenous components in organic waste water with microbes, enables to efficiently treat the waste water by denitrification.

In the following, the present invention will be described in more detail with reference to comparative examples and working examples, which however shall not limit the present invention thereto.

Measurements were made of the specific gravity of the carrier thus obtained upon swelling in water and the degree of volumetric swelling in water thereof in the following manner:

(1) Specific Gravity Upon Swelling in Water

By regarding the volume which did not change any longer when a sample was immersed in pure water at 25° C. as the volume upon complete swelling in water, from which specific gravity thereupon was determined.

(2) Degree of Volumetric Swelling

Degree of volumetric swelling was determined from the foregoing formula (III).

With regard to the inorganic filler used therein, barium sulfate powder had a particle diameter of 0.1 to 15 μm, an average particle diameter of 9.0 μm and a specific gravity of 4.3; and silica powder had a particle diameter of 7.0 to 40 μm, an average particle diameter of 15.0 μm and a specific gravity of 2.2. The compatible resin B-1 was polyurethane elastomer type F manufactured by Nisshinbo Industries, Inc., and the compatible resin B-2 was polyurethane elastomer type P manufactured by Nisshinbo Industries, Inc.

REFERENCE EXAMPLE 1

In a reaction kettle equipped with an agitator was placed 100 parts by weight of polyethylene glycol having a number average molecular weight of 2000 as the long chain diol compound. Then preliminary heating was carried out at 110° C. for one hour in an atmosphere of nitrogen so as to release the moisture in the polyethylene glycol, and thereafter the reaction kettle was set to a temperature of 130° C. Subsequently in the reaction kettle was added 25 parts by weight of 4,4'-diphenylmethane diisocyanate as the diisocyanate compound under stirring at 130° C. for 2 hours to prepare a prepolymer. Subsequently 1.19 part by weight of 1,4-butanediol as the chain length extender was added with stirring at 130° C. for one hour. After the completion of the reaction, the prepolymer was cast onto a vat which had been subjected to releasing treatment, followed by heating treatment at 100° C. for 4 hours to obtain water swellable thermoplastic polyurethane resin.

REFERENCE EXAMPLE 2

The thermoplastic polyurethane resin prepared in Reference Example 1 was allowed to cool, then crushed into small pieces, heat melted at 180 to 230° C. by the use of an heating extruder under shearing force applied thereto, and extruded through the nozzles of the extruder to prepare strands of 2.5 mm in diameter. The strands thus obtained were cut into columnar carrier of 2.5 mm in length. The resultant carrier had a specific gravity upon swelling in water of 1.012 and a degree of volumetric swelling of 850%.

EXAMPLES 1 TO 4

The procedure in Reference Example 2 was repeated to prepare a carrier, except that the compatible resin B-1 in an amount as given in Table 1 was blended with water swellable thermoplastic polyurethane resin. Thus measurements were made of the specific gravity upon swelling in water and degree of volumetric swelling in water each for the carrier thus obtained. The results are given in Table 1.

EXAMPLES 5 TO 7

The procedure in Reference Example 2 was repeated to prepare a carrier, except that the compatible resin B-1 and dehydrated barium sulfate powder each in an amount as given in Table 1 were blended with water swellable thermoplastic polyurethane resin. Thus measurements were made of the specific gravity upon swelling in water and degree of volumetric swelling in water each for the carrier thus obtained. The results are given in Table 1.

EXAMPLES 8 TO 12

The procedure in Reference Example 2 was repeated to prepare a carrier, except that the compatible resin B-2 in an amount as given in Table 1 was blended with water swellable thermoplastic polyurethane resin. Thus measurements were made of the specific gravity upon swelling in water and degree of volumetric swelling in water each for the carrier thus obtained. The results are given in Table 1.

EXAMPLES 13 TO 22

The procedure in Reference Example 2 was repeated to prepare a carrier, except that the compatible resin B-2 and dehydrated barium sulfate powder or silica powder each in an amount as given in Table 1 were blended with water swellable thermoplastic polyurethane resin. Thus measurements were made of the specific gravity upon swelling in water and degree of volumetric swelling in water each for the carrier thus obtained. The results are given in Table 1.

TABLE 1

| | Resin Component | | | | | Carrier | |
| --- | --- | --- | --- | --- | --- | --- | --- |
| | | Compatible | | Inorganic filler | | Sp. Gr. | |
| Example No. | PUR (Pt. Wt.) | Resin Kind | (Pt. Wt.) | Kind | Blending Amount (Pt. Wt.) | on swelling in water | Deg. Vol. swelling in water % |
| 1 | 80 | B-1 | 20 | — | — | 1.027 | 660 |
| 2 | 60 | B-1 | 40 | — | — | 1.063 | 420 |
| 3 | 40 | B-1 | 60 | — | — | 1.110 | 210 |
| 4 | 20 | B-1 | 80 | — | — | 1.166 | 170 |
| 5 | 20 | B-1 | 80 | BaSO$_4$ | 20 | 1.247 | 170 |
| 6 | 20 | B-1 | 80 | BaSO$_4$ | 40 | 1.420 | 150 |
| 7 | 40 | B-1 | 60 | BaSO$_4$ | 40 | 1.241 | 200 |
| 8 | 80 | B-2 | 20 | — | — | 1.034 | 650 |
| 9 | 70 | B-2 | 30 | — | — | 1.040 | 540 |
| 10 | 60 | B-2 | 40 | — | — | 1.043 | 410 |
| 11 | 40 | B-2 | 60 | — | — | 1.053 | 200 |
| 12 | 20 | B-2 | 80 | — | — | 1.065 | 160 |
| 13 | 80 | B-2 | 20 | BaSO$_4$ | 40 | 1.086 | 610 |
| 14 | 80 | B-2 | 20 | BaSO$_4$ | 60 | 1.083 | 600 |
| 15 | 80 | B-2 | 20 | BaSO$_4$ | 80 | 1.114 | 580 |
| 16 | 70 | B-2 | 30 | BaSO$_4$ | 40 | 1.084 | 520 |

TABLE 1-continued

| Example No. | Resin Component | | | Carrier | | | |
|---|---|---|---|---|---|---|---|
| | PUR (Pt. Wt.) | Compatible Resin Kind | (Pt. Wt.) | Inorganic filler Kind | Blending Amount (Pt. Wt.) | Sp. Gr. on swelling in water | Deg. Vol. swelling in water % |
| 17 | 70 | B-2 | 30 | $BaSO_4$ | 60 | 1.123 | 500 |
| 18 | 70 | B-2 | 30 | $BaSO_4$ | 80 | 1.133 | 490 |
| 19 | 70 | B-2 | 30 | $BaSO_4$ | 120 | 1.211 | 480 |
| 20 | 60 | B-2 | 40 | $BaSO_4$ | 60 | 1.141 | 460 |
| 21 | 40 | B-2 | 60 | $BaSO_4$ | 40 | 1.200 | 210 |
| 22 | 70 | B-2 | 30 | Silica | 30 | 1.082 | 490 |
| Ref. 2 | 100 | — | — | — | — | 1.012 | 850 |

{Remarks}
PUR: Polyurethane resin
Pt. Wt.: Parts by weight
Sp. Gr.: Specific Gravity
Deg. Vol.: Degree of Volumetric
$BaSO_4$: barium sulfate
$\underline{BaSO_4}$: dehydrated barium sulfate
Ref. 2: Reference Example 2

EXAMPLES 23 TO 26

The procedure in Reference Example 1 was repeated to prepare water swellable thermoplastic polyurethane resin, except that barium sulfate powder in proportions as given in Table 2 to the prospective polyurethane resin at the time of preliminary heating in the preparation of prepolymer in Reference Example 1. Subsequently, a carrier was prepared in the same manner as in Reference Example 2 by blending the resultant polyurethane resin with the compatible resin B-2 as given in Table 2. Thus measurements were made of the specific gravity upon swelling in water and degree of volumetric swelling in water each for the carrier thus obtained in not only Examples 23 to 26 but also Comparative Example 1 in which the compatible resin B-2 was not blended. The results are collectively given in Table 1.

TABLE 2

| Example No. | at PUR Preparation Time | | at Molding Time | Carrier | |
|---|---|---|---|---|---|
| | PUR (Pt. Wt.) | $BaSO_4$ (Pt. Wt.) | Compatible Resin B-2 (Pt. wt.) | Specific Gravity on swelling in water | Degree of volumetric swelling in water (%) |
| 23 | 40 | 40 | 60 | 1.178 | 205 |
| 24 | 33 | 33 | 67 | 1.189 | 170 |
| 25 | 25 | 25 | 75 | 1.189 | 165 |
| 26 | 50 | 25 | 50 | 1.114 | 310 |
| Comparative Example 1 | 100 | 100 | — | 1.082 | 830 |

{Remarks}
PUR: Polyurethane resin
Pt. Wt.: Parts by weight
$BaSO_4$: barium sulfate
$\underline{BaSO_4}$: dehydrated barium sulfate

EXAMPLE 27
(Nitrification Denitrification Test for Carrier)

By the use of the carrier as obtained in Example 15 and the nitrification denitrification apparatus as illustrated in FIG. 1, the raw water having the following composition was subjected to intermittent aeration treatment under the following operation conditions:

| Composition of raw water | Concentration (mg/L) |
|---|---|
| glucose | 61.8 |
| L-glutamic acid | 61.8 |
| Ammonium chloride | 93.2 |
| $KH_2PO_4$ | 4.3 |
| $CaCl_2.2H_2O$ | 46.3 |
| $MgSO_4.7H_2O$ | 32.4 |
| $ZnCl_2$ | 0.208 |
| $FeSO_4.7H_2O$ | 1.0 |
| EDTA.2Na | 1.8 |
| $CuSO_4.5H_2O$ | 0.51 |
| $MnCl_2.4H_2O$ | 0.072 |
| $Na_2MoO_4.2H_2O$ | 0.05 |
| $CoCl_2.6H_2O$ | 0.008 |

Volume of biotreatment tank: 20 liters
Carrier: 4 liters of carrier in Example 15
Aeration cycle: one cycle was constituted of 3 hours of aerobic aeration at a dissolved oxygen concentration of 6 mg/L, and 3 hours of anaerobic aeration under agitation with an agitation impeller.
Raw water flow rate: added at 6.67 L/hr (80 L/day) only during anaerobic aeration
Retention time: 6.0 hour
Nitrogen concentration in raw water: 30 mg-N/L
Nitrogen load: 0.12 kg-N/$m^3$-tank·day
Sludge return: returned so as to attain MLSS concentration of 2000 mg/L
Water temperature: regulated to 22° C.

In Table 3 are given the average water qualities of the treated water on and after 60th day from the start of the test.

TABLE 3

| | Raw water | Treated water in Example 27 | Treated water in Comp. Example 2 |
|---|---|---|---|
| T-BOD (mg/L) | 100 | 4.0 | 5.8 |
| T-N (mg/L) | 30 | 2.4 | 5.9 |
| $NH_4$-N (mg/L) | 24.4 | <0.1 | 1.8 |
| $NO_3$-N + $NO_2$-N (mg/L) | ND | 1.0 | 3.9 |

COMPARATIVE EXAMPLE 2
(Nitrification Denitrification Test Without the Use of a Carrier The procedure in Example 27 was repeated to carry out the intermittent aeration test except that none of carrier was added to the biotreatment tank and the MLSS concentration was set to 3000 to 3500 mg/L. The average water qualities of the treated water on and after 60th day from the start of the test are given in Table 3.

In this test, sludge floatation was observed in the settling tank on and after 10th day from the start of the test, and the suspended sludge flowed out. The water qualities of the treated water in both the nitrification and the denitrification steps was not stable, showing a T-N removal rate of about 80%.

What is claimed is:

1. A bioreactor carrier which comprises a (A) water swellable thermoplastic resin and a (B) compatible resin with said resin as the component (A), wherein the degree of volumetric swelling of said carrier is controlled within the range of 120 to 3000%.

2. A bioreactor carrier which comprises a (A) water swellable thermoplastic resin, a (B) compatible resin with said resin as the component (A), and a (C) inorganic filler, wherein the degree of volumetric swelling of said carrier is controlled within the range of 120 to 3000%, and that the specific gravity of said carrier on swelling in water is controlled within the range of 1.02 to 2.12.

3. The bioreactor carrier according to claim 1, wherein the water swellable thermoplastic resin as the component (A) is water swellable thermoplastic polyurethane resin.

4. The bioreactor carrier according to claim 2, wherein the water swellable thermoplastic resin as the component (A) is water swellable thermoplastic polyurethane resin.

5. The bioreactor carrier according to claim 2, wherein the inorganic filler as the component (C) has an average particle diameter in the range of 0.1 to 50 μm and a specific gravity of at least 1.5.

6. The bioreactor carrier according to claim 2, wherein the component (C) is contained in an amount of 1 to 350 parts by weight of based on 100 parts by weight of the total sum of the components (A) and (B).

7. The bioreactor carrier according to claim 1, wherein the content ratio by weight of the component (A) to the component (B) is in the range of 90:10 to 10:90.

8. The bioreactor carrier according to claim 2, wherein the content ratio by weight of the component (A) to the component (B) is in the range of 90:10 to 10:90.

9. A process for denitrifying treatment of organic waste water which comprises nitrifying and denitrifying nitrogen components in the organic waste water with microbes by the use of the bioreactor carrier as set forth in claim 1.

10. A process for denitrifying treatment of organic waste water which comprises nitrifying and denitrifying nitrogen components in the organic waste water with microbes by the use of the bioreactor carrier as set forth in claim 2.

11. The process for denitrifying treatment of organic waste water according to claim 9; wherein use is made of said bioreactor carrier in both a nitrifying step and a denitrifying step alternately and repeatedly.

12. The process for denitrifying treatment of organic waste water according to claim 10, wherein use is made of said bioreactor carrier in both a nitrifying step and a denitrifying step alternately and repeatedly.

* * * * *